(12) United States Patent
Wang et al.

(10) Patent No.: US 10,642,027 B2
(45) Date of Patent: May 5, 2020

(54) 3D MEMS SCANNER FOR REAL-TIME CROSS-SECTIONAL ENDOMICROSCOPY

(71) Applicant: THE REGENTS OF THE UNIVERSITY OF MICHIGAN, Ann Arbor, MI (US)

(72) Inventors: Thomas D. Wang, Ann Arbor, MI (US); Haijun Li, Ann Arbor, MI (US); Xiyu Duan, Ann Arbor, MI (US); Zhen Qiu, Menlo Park, CA (US); Kenn Oldham, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/781,065

(22) PCT Filed: Dec. 8, 2016

(86) PCT No.: PCT/US2016/065677
§ 371 (c)(1),
(2) Date: Jun. 1, 2018

(87) PCT Pub. No.: WO2017/100485
PCT Pub. Date: Jun. 15, 2017

(65) Prior Publication Data
US 2018/0356629 A1    Dec. 13, 2018

Related U.S. Application Data

(60) Provisional application No. 62/264,645, filed on Dec. 8, 2015.

(51) Int. Cl.
*G02B 26/08* (2006.01)
*G02B 21/00* (2006.01)
(Continued)

(52) U.S. Cl.
CPC .......... *G02B 26/0841* (2013.01); *A61B 1/313* (2013.01); *A61B 5/0068* (2013.01);
(Continued)

(58) Field of Classification Search
CPC .............. G02B 26/0833; G02B 26/001; G02B 26/0841; G02B 26/02; G02B 26/06
(Continued)

(56) References Cited

U.S. PATENT DOCUMENTS

| 7,388,700 B1 | 6/2008 | Odhner | |
|---|---|---|---|
| 2003/0223679 A1* | 12/2003 | Mala | ..................... B81B 3/0062 385/18 |

(Continued)

OTHER PUBLICATIONS

International Search Report and Written Opinion from International Application No. PCT/US2016/065677 dated Feb. 17, 2017.

*Primary Examiner* — Mohammed A Hasan
(74) *Attorney, Agent, or Firm* — Marshall, Gerstein & Borun LLP

(57) ABSTRACT

An optical probe scanning assembly for use in an optical probe includes a mirror assembly that focuses an illumination beam path and a collection beam path at a region of interest within the sample. The illumination beam and the collection beam overlap to form a confocal beam region. The mirror assembly is movable in an x-axis direction and in a y-axis direction to scan the confocal beam region within the sample. The scanning assembly further includes a scanning suspension system including a gimbal assembly connected to the mirror assembly to allow the mirror assembly to rotate about one or more axes. The mirror is thereby adapted to scan along at least two different orthogonal planes, one of which extends vertically into the sample.

17 Claims, 10 Drawing Sheets

(51) Int. Cl.
  *G02B 23/24*  (2006.01)
  *B81B 3/00*  (2006.01)
  *A61B 5/1459*  (2006.01)
  *A61B 1/313*  (2006.01)
  *A61B 5/00*  (2006.01)
  *G02B 6/26*  (2006.01)
  *G02B 26/10*  (2006.01)

(52) U.S. Cl.
  CPC .......... *A61B 5/0073* (2013.01); *A61B 5/1459* (2013.01); *B81B 3/0021* (2013.01); *G02B 6/26* (2013.01); *G02B 21/0048* (2013.01); *G02B 23/24* (2013.01); *G02B 26/103* (2013.01)

(58) Field of Classification Search
  USPC ........................................................ 359/291
  See application file for complete search history.

(56) References Cited

U.S. PATENT DOCUMENTS

| | | | | |
|---|---|---|---|---|
| 2006/0152106 A1* | 7/2006 | Yan | ...................... | G02B 26/085 |
| | | | | 310/309 |
| 2011/0125029 A1* | 5/2011 | Wang | .................. | A61B 5/0068 |
| | | | | 600/476 |

* cited by examiner

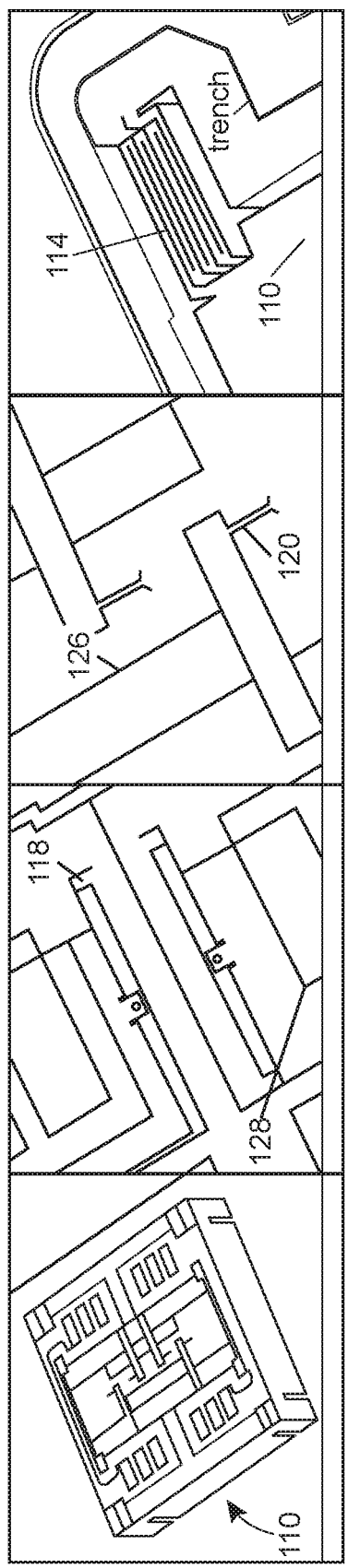

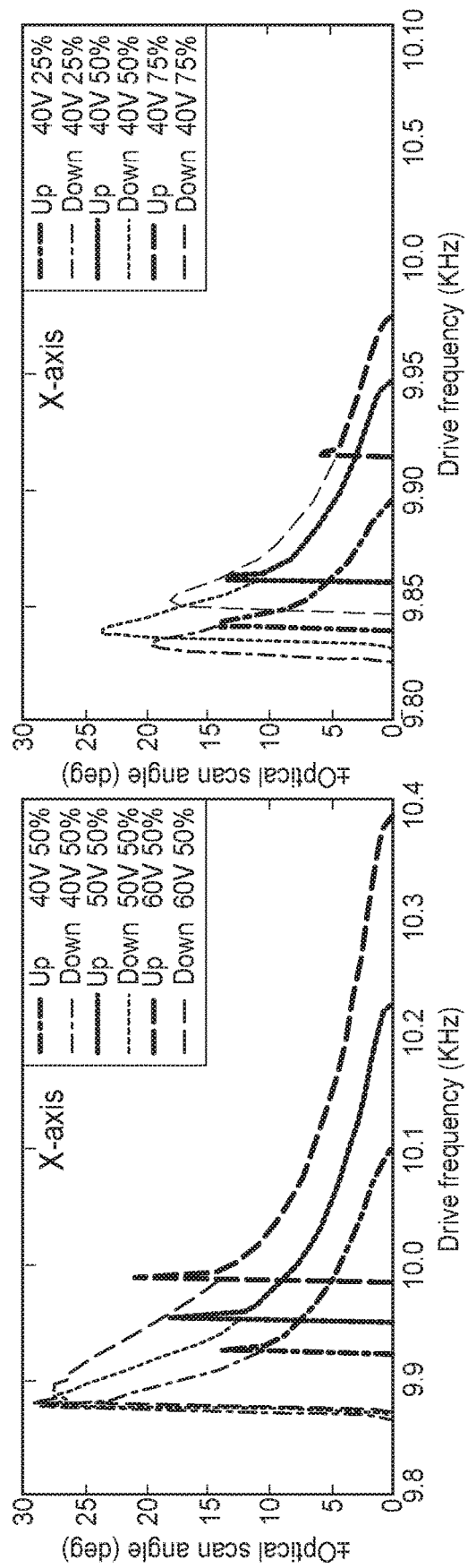
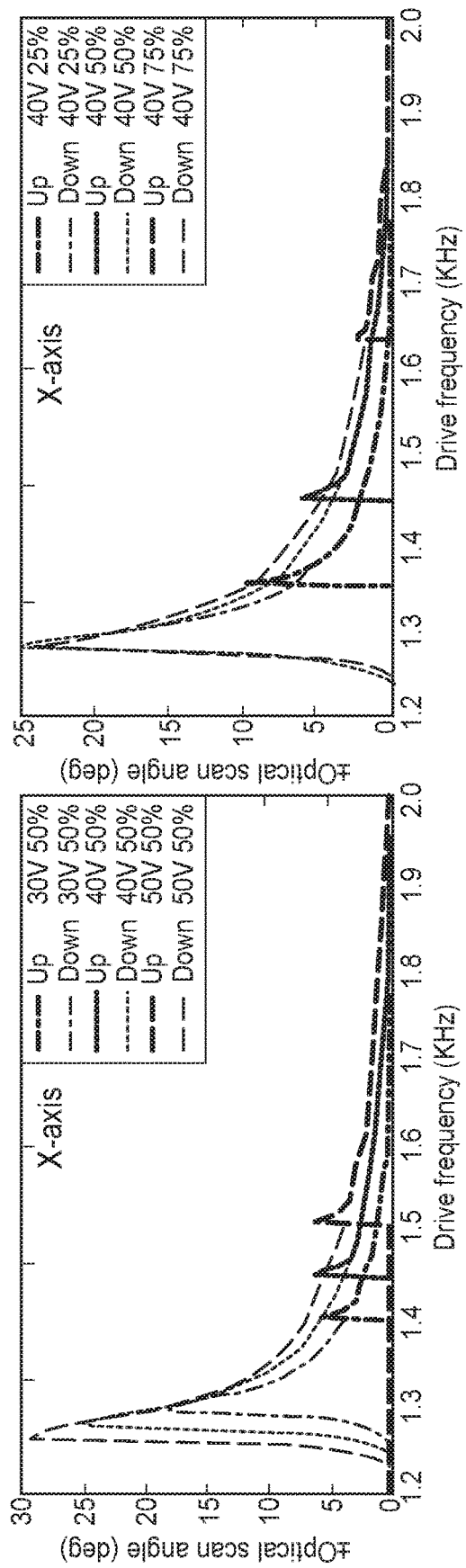
FIG. 5A
FIG. 5B
FIG. 5C
FIG. 5D

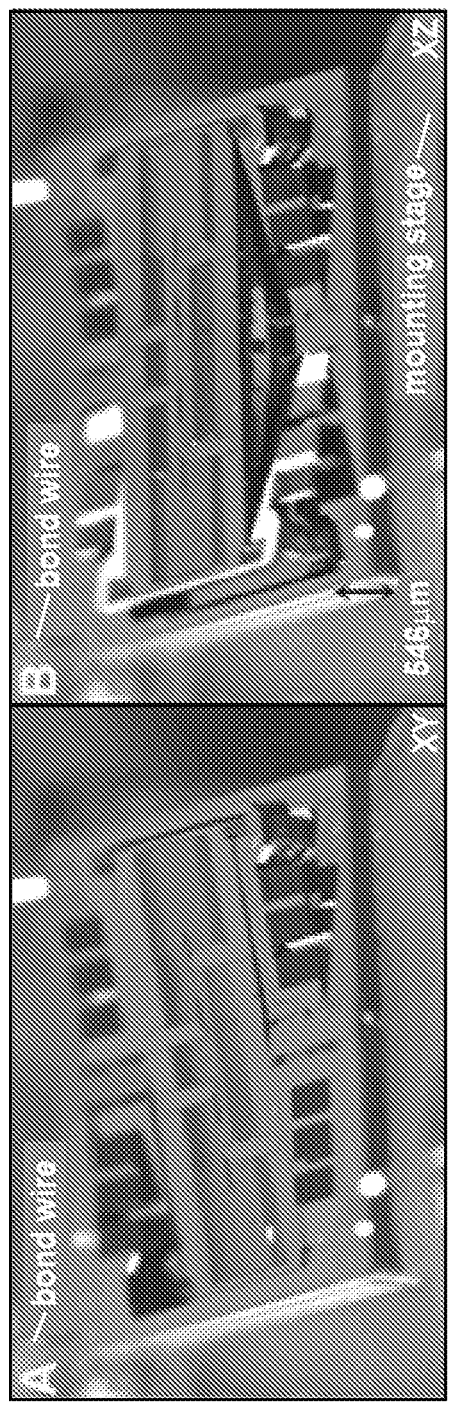

3D MEMS SCANNER FOR REAL-TIME CROSS-SECTIONAL ENDOMICROSCOPY

CROSS REFERENCE TO RELATED APPLICATIONS

This application claims the benefit of U.S. Provisional Application No. 62/264,645, entitled "3D MEMS Scanner for Real-Time Cross-Sectional Endomicroscopy," filed on Dec. 8, 2015, the entirety of which is herein expressly incorporated by reference.

STATEMENT OF GOVERNMENT INTEREST

This invention was made with government support under CA142750 awarded by the National Institutes of Health. The government has certain rights in the invention.

FIELD OF THE DISCLOSURE

The disclosure relates generally to techniques for imaging tissue using an optical instrument and, more particularly, to techniques for allowing real-time scanning using an optical instrument.

BACKGROUND

The brief description of related technology provided herein is for the purpose of generally presenting the context of the disclosure. Work of the presently named inventor, to the extent it is described in this brief description of related technology section, as well as aspects of the description that may not otherwise qualify as prior art at the time of filing, are neither expressly nor impliedly admitted as prior art against the present disclosure.

Endomicroscopes perform optical sectioning and can collect in vivo images in the epithelium of hollow organs, such as colon, with sub-cellular resolution. This thin layer of tissue has high metabolic activity, and is the origin of many cancers. Under normal conditions, a vertical dimension (perpendicular to tissue surface) of the epithelium is approximately 400 µm in depth. Current clinical microscopes use a flexible optical fiber coupled to an objective lens in a single axis configuration. As a result, current clinical microscopes visualize solely in horizontal planes (i.e., parallel to tissue surface). However, imaging in the vertical plane is of great importance because epithelial cells naturally differentiate in this vertical direction. Additionally, cancer cells originate in this layer and invade downwards, thus a vertical view can provide the ability to accurately localize where the disease is occurring relative to the tissue surface, and pathologists could this orientation to stage progression of early cancer.

Imaging in the vertical plane benefits from an optical detection method with sufficient dynamic range to detect light over many orders of magnitude because of cumulative effects from tissue absorption and scattering. In some approaches, a dual axes confocal architecture is used that employs two distinct beams and objectives oriented off-axis to illuminate and collect light, and provide high dynamic range that rolls off exponentially in the axial (Z-axis) direction. Such designs use low numerical aperture objectives to produce a long working distance that provides space for a miniature scanner to be located in a post-objective position. This configuration allows for the optics to be scaled down to millimeter dimensions and to generate a very large field-of-view (FOV) compared to other endomicroscope designs, which have been used to demonstrate vertical cross-sectional images using a 10 mm diameter instrument with a large, bulky piezoelectric (PZT) actuator to perform axial scanning.

There is, however, an ongoing need for a miniature scanner that provides large angular deflections and sizable axial displacements to image in either the horizontal or vertical plane. Microscanners based on microelectromechanical systems (MEMS) technology have been developed and widely used in endomicroscopy. Yet, most MEMS scanners produce in-plane 2D scanning to only collect horizontal images. An actuator must either move the objective lens or scan out-of-plane to collect vertical images. Several MEMS-based 3D scanners have been developed that can enable tip-tilt-piston motions, but these devices suffer from coupling between different directions of motion and/or cannot reach as high scanning speeds as desired.

Other scanning technologies are being developed for use in endomicroscopes to perform in vivo imaging. While some designs can provide adequate lateral in vivo scanning, the designs have limitations in ability to scan with large out-of-plane displacement. Shape memory alloy (nitinol) based actuators, for example, are used in first generation confocal endomicroscopes to provide a large axial displacement (>250 µm), but these devices are slow and suffer from hysteresis. Other MEMS-based electrostatic scanners have been developed with fast response times at low voltages but have not achieved adequate Z-axis motion. Electrothermal devices can provide large axial displacements (>600 µm) at low voltages (~5 V) but the response time is too slow for in vivo imaging. Piezoelectric scanners can achieve large DC displacements, but 3D fast-axis scanning frequencies are limited, and fabrication complexity is high. Electromagnetic scanners have been developed with fast response times and good displacement, but the technology is difficult to scale down in size for most endomicroscopy applications.

SUMMARY

To address the foregoing, the present application describes an integrated, monolithic MEMS scanner capable of collecting images in either the horizontal or vertical plane while achieving a depth that spans the epithelium of hollow organs.

The techniques herein may be used in an optical probe capable of targeted imaging of molecular changes that occur in transformed cells and tissues, e.g., those that have progressed to cancer in the colon, breast, etc., providing critical imaging targets. Any number of targets may be imaged with MEMS scanners in accordance with the present techniques. Improvements in imaging technology for identifying and localizing the presence of these cancer biomarkers may dramatically improve the ability to perform early detection, risk stratification, and therapeutic monitoring of cancer. Generally speaking, molecular probes have demonstrated potential for detecting early neoplastic changes in small animal models by their high binding specificity to pre-malignant targets. As used herein, the term "specificity" means that the molecular probe can identify, bind, and/or interact with one target with a higher affinity and/or avidity compared to all other targets. For example, the use of monoclonal antibodies to bind cell surface targets in tumors in the colon and breast for diagnosis and therapy has been demonstrated. In addition, proteases, or proteolytic enzymes that are important targets that play an important role in cell proliferation, invasion, apoptosis, angiogenesis, and metastasis, can be more readily identified. Example proteases include cathepsin B and matrix metalloproteinases. Molecular probes that bind to these targets can be radiolabeled for detection on whole body imaging, such as with PET and SPECT, and can be fluorescence labeled for detection on endoscopy and microscopy.

The dual-axes architectures described herein provide an imaging geometry capable of overcoming tissue scattering issues of conventional imaging modalities, while providing superior dynamic range and 3D scanning. This orientation is valuable for visualizing the epithelium (and other tissue) because this tissue differentiates in the plane perpendicular to the tissue surface. Dual-axis architectures also provide for increased imaging depth when compared to multi-photon architectures, and can also use less complex optical designs that provide easier fiber connectivity.

In accordance with an example of the disclosure, an optical probe scanning assembly for use in an optical probe having a housing having a proximal end and a distal end positioned at a sample, the scanning assembly comprises: a mirror assembly configured to focus an illumination beam path and a collection beam path at a region of interest within the sample where the illumination beam and the collection beam overlap to form a confocal beam region, the mirror assembly being movable in an x-axis direction and in a y-axis direction to scan the confocal beam region within the sample; and a scanning suspension system comprising a gimbal assembly connected to the mirror assembly to allow the mirror assembly to rotate about one or more axes, and such that the mirror is to scan along at least two different orthogonal planes, one of which extends vertically into the sample region.

BRIEF DESCRIPTION OF THE DRAWINGS

For a more complete understanding of the disclosure, reference should be made to the following detailed description and accompanying drawing figures, in which like reference numerals identify like elements in the figures, and in which:

FIG. 1B illustrates operation about an X-axis, FIG. 1C illustrates operation about a Y-axis, and FIG. 1D illustrates operation about a Z-axis in accordance with various embodiments;

FIGS. 4A-4D are perspective views of a complete scanning assembly, with FIG. 4B illustrating an outer, trapezoidal spring assembly, FIG. 4C illustrating an inner, torsional spring assembly, and FIG. 4D illustrating a serpentine spring assembly in accordance with various embodiments;

FIGS. 5A-5F are frequency response results for X-, Y-, and Z-axes which illustrate varying optical scan angles at different voltages in accordance with various embodiments;

FIGS. 6A and 6B are perspective views of the optical scanner illustrating angular tilting of the mirror and out-of-plane motion of the mirror in accordance with various embodiments;

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, techniques for the design, fabrication, and performance of a compact integrated monolithic three-dimensional (3D) MEMS scanner having dimensions which can be housed within an endoscopic device are provided. In an example, the 3D MEMs scanner can be sized to dimensions below approximately 10×10 mm$^2$, below approximately 5×5 mm$^2$, below approximately 4×4 mm$^2$, and so on.

The 3D MEMS scanning techniques described herein are capable of producing both large angular deflections and out-of-plane displacement. For example, optical deflection angles of greater than approximately ±10°, greater than approximately ±15°, greater than approximately ±25°, and so on, are achievable in the X-axis and Y-axis motion. The 3D MEMS scanner techniques described herein can achieve such operating conditions with scanning along the z-axis at depths greater than approximately 200 μm, greater than approximately 300 μm, greater than approximately 400 μm, greater than approximately 500 μm, and so on.

Scanning at full 3D volumes at fast scan rates across the volume is achievable. For example, scanning rates of greater than 1 frame per second, greater than 2 frames per second, greater than 5 frames per second, greater than 10 frames per second, and so on, are achievable. When packaged in a dual axes confocal endomicroscope, vertical and horizontal cross-sectional images can be collected seamlessly in tissue with large field of view (FOV).

Figure 8:
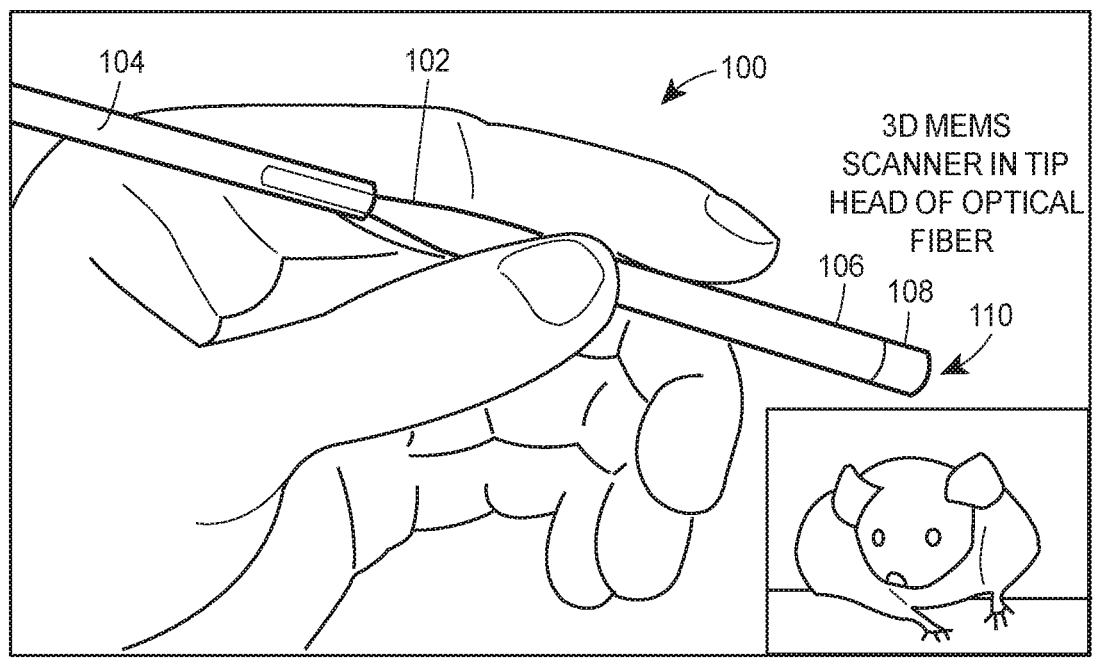
FIG. 8 is an optical probe having a proximal end with an umbilical and a distal end having a tip which houses a 3D MEMS scanner in accordance with various embodiments.

As illustrated in the figures, and with initial reference to FIG. 8, a dual-axis optical probe 100 includes a proximal end 102 with an umbilical 104 and distal end 106 having a tip 108 within which is mounted an integrated, monolithic electrostatic 3D MEMS scanner 110. As illustrated in FIGS. 1A-1D, the 3D MEMS scanner 110 has a mirror geometry that is capable of use in a dual axes endomicroscope, and is built on a gimbal frame 111 that is coupled to U-shaped suspensions 112 or lever arms via a number of serpentine springs 114 located at each corner. The suspensions 112 act as a lever to either rotate the mirror or reflectors 116 around the outer, Y-axis or create out-of-plane displacement along the Z-axis. In some examples, the mirror 116 is a parabolic mirror. Use of the gimbal frame 111 reduces cross-talk between the axes, and allows the mirror to rotate to scan along multiple different orthogonal planes.

The 3D MEMS scanner 110 includes a number of springs, including one or more outer springs 118 and one or more inner springs 120 which are used in facilitating the 3D scanning control. One or more outer actuators 122 may be coupled to a controller (not shown) for receiving signals for controlling operation of the outer spring 118. Similarly, the 3D MEMS scanner 110 includes one or more inner actuators 124 for controlling operation of the inner spring 120 in response to an external control.

The 3D MEMS scanner 110 uses inner electrostatic comb-drives 126 to provide rotation about the X-axis (i.e., using the inner spring 120 and drives) and outer electrostatic comb-drives 128 to provide rotation about Y-axis (i.e., using the outer spring 118 and drives). Each of the comb-drives 126, 128 include a number of comb-fingers which are patterned in the device layer and are alternately movable and stationary. In some examples, the comb-drives 126, 128 have a gap of 5 µm. Other examples are possible.

Figure 1A:
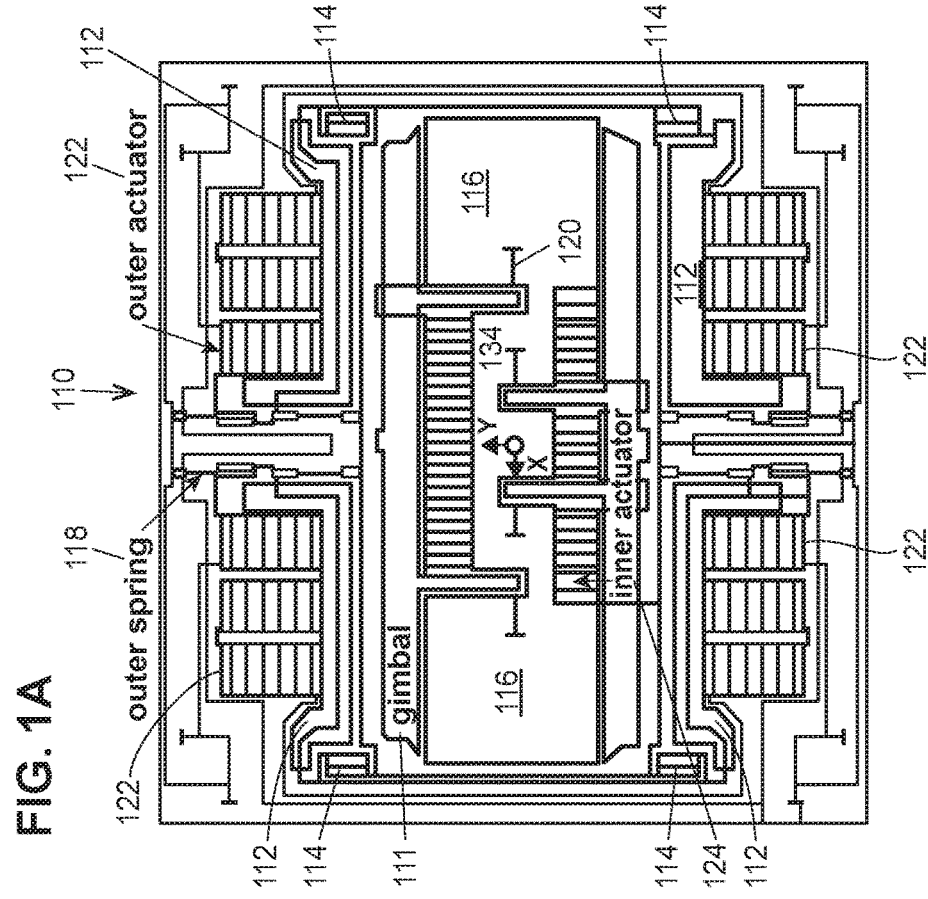
FIGS. 1A-1D are schematic views of an optical scanner having three degrees of freedom, where
Figure 1B:
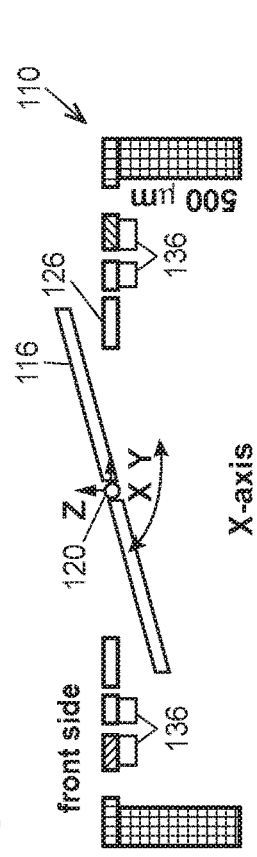
Figure 1C:
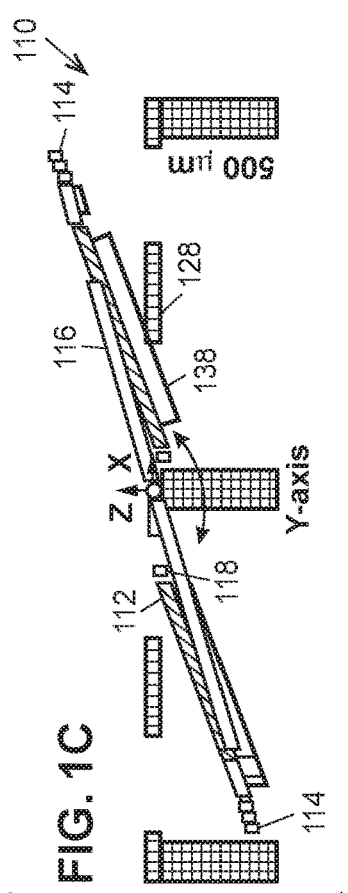
Figure 1D:
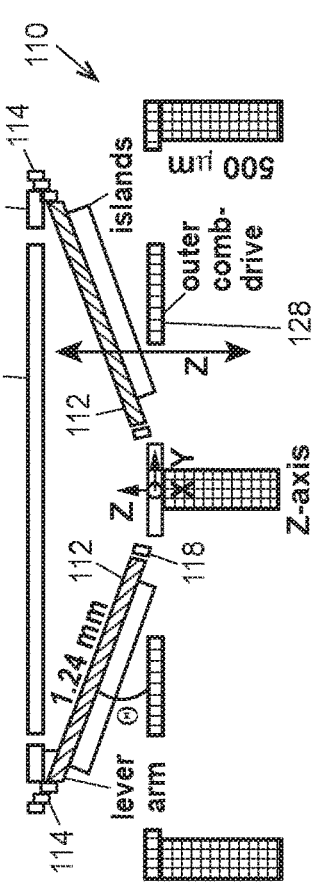

Operation of the 3D MEMS scanner 110 is based on parametric resonance to achieve large mechanical actuation. A controller (not shown) is coupled to the actuators 122, 124 and provides one or more drive signals at a frequency at or near $2\omega_0/n$ (where $\omega_0$ is the natural frequency of each mode, and n is an integer $\geq 1$). FIG. 1B illustrates rotation of the scanner 110 about the X-axis, and FIG. 1C illustrates rotation of the scanner 110 about the Y-axis. Accordingly, the combination of this movement creates lateral, or X-Y scanning movement. FIG. 1D illustrates operation of the scanner 110 to generate Z-axis displacement.

The 3D MEMS scanner 110 includes a cavity that is approximately 500 µm deep on the back side of the substrate 130 to provide for vertical displacement while the mirror 116 has a large angle of deflection. Trenches having both deep and narrow dimensions are etched in the device layer to electrically isolate drive signals between the inner and outer comb-drives 126, 128. Back side islands 132 are etched to provide mechanical support for the gimbal 111.

Figure 2A:
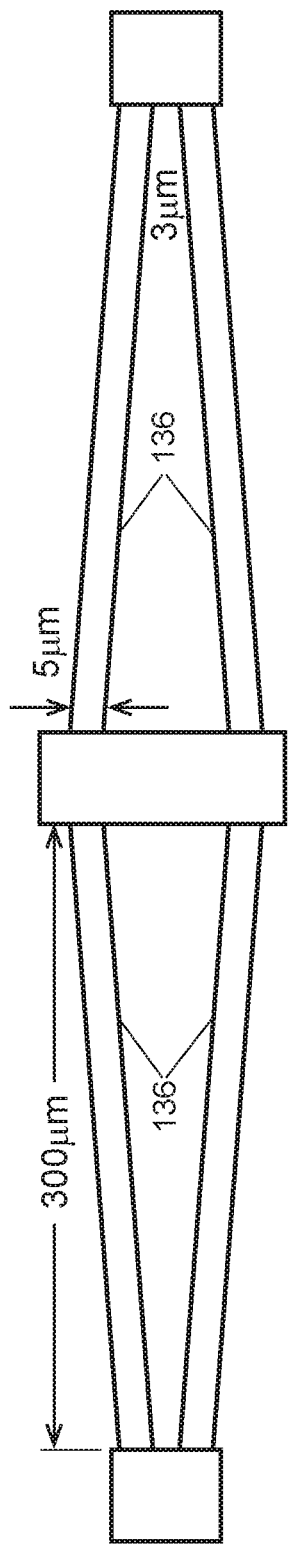
FIGS. 2A-2C are schematic views of the spring geometry of the optical scanner of FIGS. 1A-1D in accordance with various embodiments.

Resonant frequency in the X-, or inner, axis is determined by the inner springs 120. In the illustrated example, the inner springs 120 are in the form of four torsional springs, however it is understood that any number and/or type of spring can be used. In an example, the torsional springs have dimensions of approximately 200×6.5×45 µm³ and are arranged in-line along the length of the strut 134. In an example, the set of inner springs 120 are able to achieve a resonant frequency of ~5 kHz for fast scanning in the X-axis. The resonant frequency in the Y-, or outer, axis is determined by the outer springs 118. In the illustrated example, the outer springs 118 are in the form of four springs which include two symmetric pairs or sets of beams 136 oriented in a trapezoidal geometry. As shown in FIG. 2A, the beams 136 connect the suspension 112 to anchors in the substrate 130.

The illustrated configuration reduces stress on the springs to allow for greater axial displacement and to counteract "pull-in" effect from non-linear motions generated by large electrostatic forces. As an example, for the Y-axis, the outer springs 118 are dimensioned to achieve a resonance frequency of approximately 0.636 kHz. When a drive signal to the outer comb-drives 128 approaches a frequency near twice that of this eigenmode, or natural frequency, the outer comb-drives 128 rotate the suspension 112 (and thus, the mirror 116) to allow slow scanning in the horizontal plane.

In some examples, for displacement along the Z-axis, the scanner 110 has a resonant frequency of approximately 0.465 kHz. At twice this drive frequency, the suspensions 112 act as levers that displace the mirror 116 with a large out-of-plane motion in the vertical plane. Thus, by tuning the drive frequency, the mode of the scanner may be "switched" to image in either the horizontal or vertical plane.

In the illustrated examples, the 3D MEMS scanner 110 can achieve greater than 400 µm of axial displacement of the optical focus to image the full extent of a normal epithelium. By using long suspensions or lever arms (e.g., approximately 1.24 mm as defined by the distance between the outer springs 118 and the serpentine springs 114; see FIG. 1D), large axial displacement is achieved given chip dimension. In an example, three columns of outer comb-drives 128 are used to generate a sufficiently large force to produce angular deflections greater than approximately 24° (±12°) and achieve out-of-plane mirror 116 motion greater than approximately 400 µm (±200 µm).

Figure 2C:
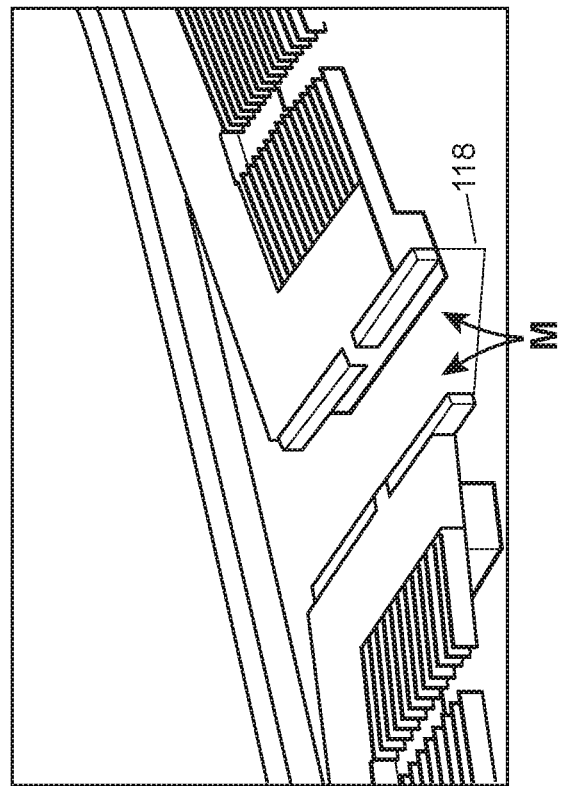
Figure 2B:
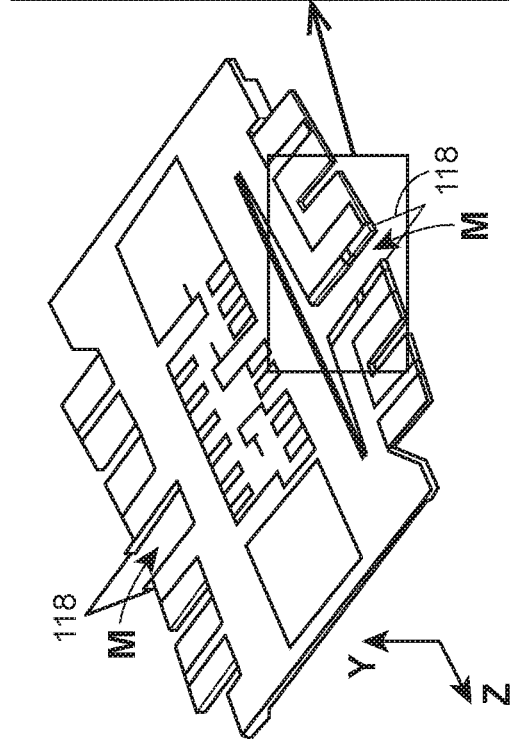

Large axial displacements may introduce structural stresses that can weaken device integrity. Accordingly by using a finite element model (FEM) using ANSYS software, the distribution of stress throughout the scanner is assessed. This model indicates a maximum stress of approximately 750 MPa at either end of the outer springs 118 (denoted by reference character "M" in FIGS. 2B and 2C) with ±400 µm axial displacement. This value is below the maximum limit for fracture strength for this material (single crystal silicon). Accordingly, the outer spring 118 can safely and repetitively achieve large out-of-plane displacements.

By carefully choosing resonant frequencies, interference is minimized from parasitic vibrations that can distort the image. This undesirable motion results from either mechanical or capacitive coupling of super-harmonic or sub-harmonic frequencies near the drive frequency. Natural frequencies of each mode are separated from adjacent natural or harmonic frequencies of other modes with a spacing of $\Delta\omega \geq 0.05\omega$. Table 1 below illustrates results of the FEM modal analysis for the first 10 eigenmodes. The 2/n order harmonic frequencies of each eigenmode are shown. The first order (n=2) results represent the Z-axis (out-of-plane) translational mode (465 Hz), the Y-axis torsional mode (636 Hz), and the X-axis torsional mode (4926 Hz), respectively.

TABLE 1

Modal analysis for 3D scanner

| | Eigenmodes | | | | | | | | | | |
|---|---|---|---|---|---|---|---|---|---|---|---|
| n | 1 | 2 | 3 | 4 | 5 | 6 | 7 | 8 | 9 | 10 | |
| 1 | 930 | 1272 | 3112 | 6768 | 9852 | 10654 | 11244 | 17478 | 17788 | 18590 | frequency (Hz) |
| 2 | 465 | 636 | 1556 | 3384 | 4926 | 5327 | 5622 | 8739 | 8894 | 9295 | |

TABLE 1-continued

Modal analysis for 3D scanner

| | Eigenmodes | | | | | | | | | |
|---|---|---|---|---|---|---|---|---|---|---|
| n | 1 | 2 | 3 | 4 | 5 | 6 | 7 | 8 | 9 | 10 |
| 3 | 310 | 424 | 1037 | 2256 | 3282 | 3551 | 3748 | 5826 | 5929 | 6197 |
| 4 | 233 | 313 | 778 | 1692 | 2463 | 2664 | 2811 | 4370 | 4447 | 4648 |
| 5 | 186 | 254 | 622 | 1354 | 1970 | 2131 | 2249 | 3496 | 3558 | 3718 |

FEM analysis for the optimized scanner design shows results for first ten eigenmodes. The eigenmodes for n=2 represent the first set of excitation frequencies used with parametric resonance. The table illustrates approximate values for exciting the Z (465 Hz), Y (636 Hz), and X (4926 Hz) axes (shown in bold).

Figure 3A:
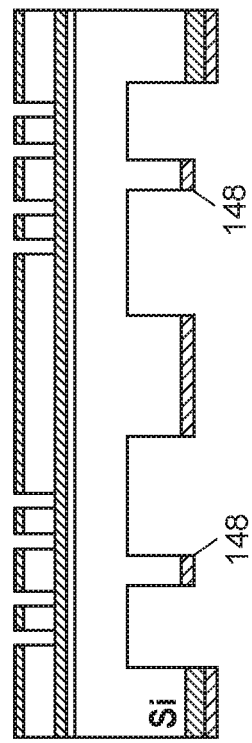
FIGS. 3A-3F are fabrication illustrations of the scanner of FIGS. 1A-1D in accordance with various embodiments.

FIGS. 3A-3F illustrate an example fabrication process for the 3D MEMS scanner 110. The 3D MEMS scanner 110 is fabricated using a three-step (i.e., 3 mask) deep reactive-ion etch (DRIE) process. As illustrated in FIG. 3A, the process begins with a silicon-on-insulator (SOI) wafer 140 that includes an approximately 45 μm silicon device layer 142, 1 μm buried oxide (BOX) layer 144, and approximately 500 μm silicon handle layer. A plasma-enhanced chemical vapor deposition (PECVD) is used to deposit approximately 0.5 and approximately 2.5 μm silicon oxide ($SiO_2$) films on the front and back surfaces of the SOI wafer 140, respectively, to serve as hard masks to protect the wafer 140 during fabrication.

Figure 3B:
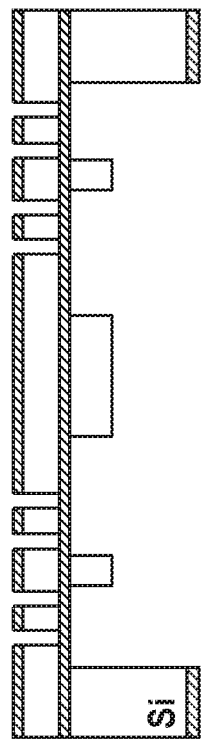

The first mask is used to pattern the upper oxide layer and define the front side scanner structures, including the mirrors 116, gimbal 111, comb-drive actuators 122, 124, and springs 118, 120. As seen in FIG. 3B, a layer of photoresist (PR) 146 is first spin-coated on the front side of the SOI wafer 140, exposed, then developed. A reactive-ion-etch (RIE) process is performed to etch the exposed PECVD oxide layer. Next, a DRIE process is used to etch the exposed silicon on the device layer.

Figure 3C:
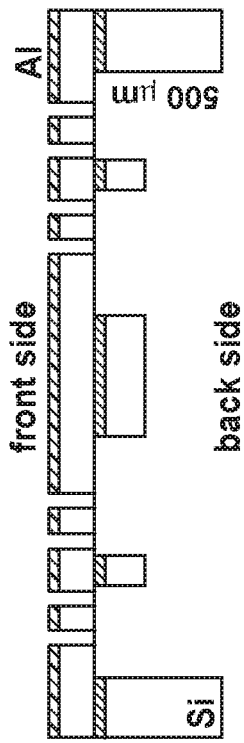

The second mask is used to define the back side scanner structures needed to provide mechanical support and to produce the cavity for mirror 116 displacement in the Z-axis. As illustrated in FIG. 3C, a layer of photoresist 146 is spin-coated on the back side of the SOI wafer, exposed, and developed. An RIE process was performed to etch the exposed back side PECVD oxide.

Figure 3D:
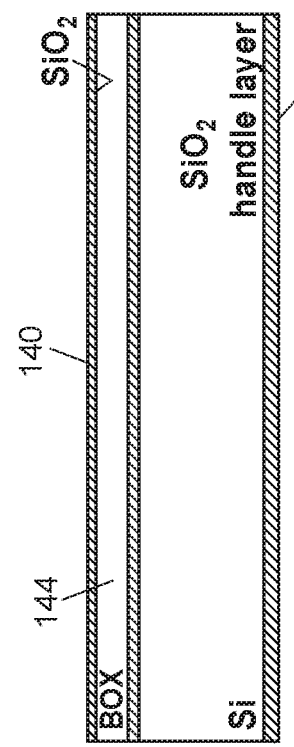
Figure 3E:
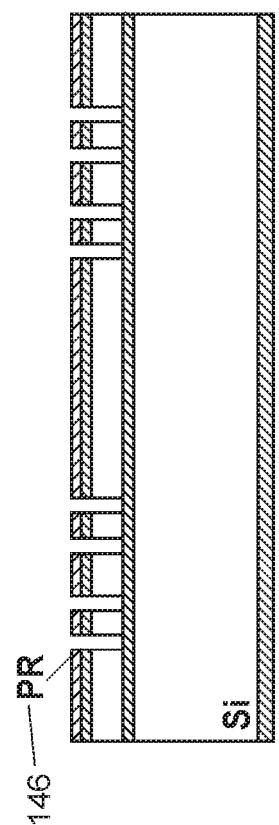
Figure 3F:
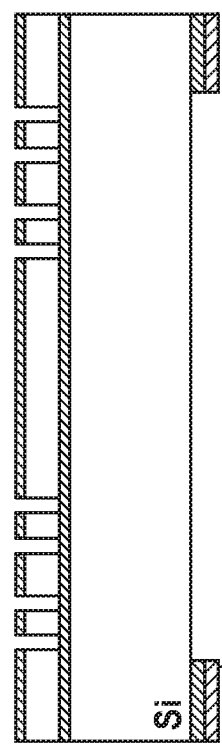

The third mask is used to pattern the back side islands 148 illustrated in FIG. 3D. A 2-step DRIE process with an in situ photoresist plasma $O_2$ ashing process is used to form the back side structures, which include the substrate frame 130, the cavity, and back side islands 148 with a thickness of ~120±20 μm (as illustrated in FIG. 3E). After removing the exposed BOX layer and the PECVD oxide layers with buffered hydrofluoric acid (BHF) wet etching, the movable structures are released by rinsing with isopropyl alcohol (IPA) followed by drying. Last, as illustrated in FIG. 3F, an approximately 70 nm layer of aluminum (Al) film is deposited onto the front side silicon to produce highly reflective surfaces with greater than approximately 85% reflectivity from approximately 200-900 nm while having minimal defects.

3D MEMS scanner 110 performance is verified by packaging the device in a 10 mm diameter dual axes confocal fluorescence endomicroscope. Fluorescence images were collected by tuning the drive frequency to "switch" between vertical (XZ) and horizontal (XY) planes. Horizontal cross-sectional images were collected at various depths using a bulk PZT actuator.

Scanning electron micrographs (SEMs) of an example, fabricated 3D MEMS scanner 110 are illustrated in FIGS. 4A-4D. The integrated, monolithic scanner has a compact chip size with overall dimensions of approximately 3.2×2.9 $mm^2$ that can fit within an approximately 5.5 mm diameter dual axes endomicroscope. As seen in FIG. 4A, the mirror 116 includes two reflective surfaces etched on the front side of the substrate. The mirror 116 surfaces may be planar or have a radius of curvature. In the illustrated example, the mirror surfaces have a radius of curvature of approximately 2.0 m and a root mean square (RMS) roughness of approximately 2 nm. As illustrated in FIGS. 4B-4D, the outer trapezoidal, inner torsional, and serpentine springs are shown in greater detail.

Figures 5E, 5F:
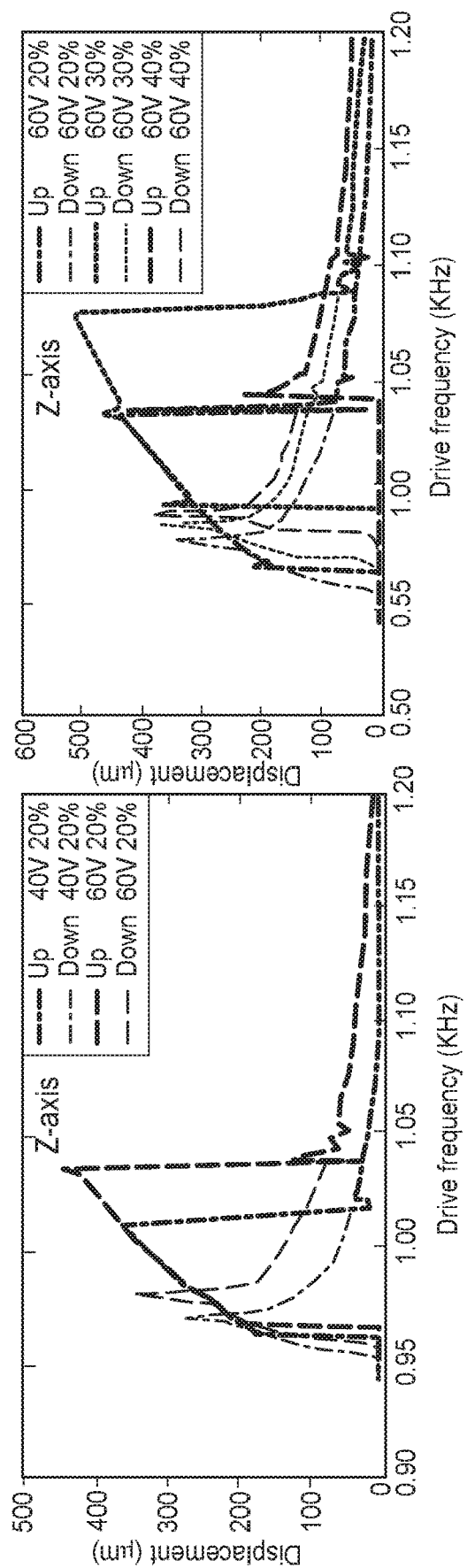

As illustrated in FIGS. 5A-5F, angular deflection and out-of-plane displacement are measured to characterize frequency response of the 3D MEMS scanner 110. Optical scan angles in the X-axis at drive voltages between approximately 40-60$V_{pp}$ and 50% duty cycle are shown in FIG. 5A, and optical scan angles in the X-axis at drive voltages at approximately 40$V_{pp}$ and 25-75% duty cycle are shown in FIG. 5B. As illustrated in FIG. 5C, the optical scan angle in the Y-axis at drive voltages between approximately 30-50$V_{pp}$ and 50% duty cycle is shown, and optical scan angles in the Y-axis at drive voltages at approximately 40$V_{pp}$ and 25-75% duty cycle are shown in FIG. 5D. Large angular deflections up to approximately ±27° and ±28.5° are achieved in the X-and Y-axes, respectively. A softening characteristic of the frequency response was observed when sweeping either from low-to-high frequency (upsweep) or from high-to-low frequency (downsweep).

Scanner displacement along the Z-axis with a square-wave drive signal from 40 to 60$V_{pp}$ and 20% duty cycle is shown in FIG. 5E. At approximately 60$V_{pp}$, a stable high gain region (indicated by the "Up" line) near 1 kHz is observed with upsweep but not with downsweep. As illustrated in FIG. 5F, a maximum amplitude of approximately 510 μm (solid green) is observed with upsweep at 30% duty cycle. Along the Z-axis, the scanner shows a non-linear mixed stiffening-softening characteristic when driven by a pulsed signal with various duty cycles. A high-speed camera is used to visualize scanner operation in the XY and XZ planes. Individual frames show large angular deflection about the Y-axis (see FIG. 6A), and large out-of-plane displacement in the Z-axis (see FIG. 6B). By comparison, the thickness of the 3D MEMS scanner 110 is 546 μm. As previously discussed, the device is seated on a mounting stage having a cavity which allows for large axial displacements.

In an example, the 3D MEMS scanner can collect confocal images from human colonic mucosa ex vivo with $\lambda_{ex}$=785 nm excitation. The tissues were stained with IRDye 800. Fluorescence images were collected at 5 frames per second in either the vertical (XZ; see FIG. 7A) or horizontal (XY; see FIG. 7B) plane with dimensions of either 1050× 410 μm² or 1050×1050 μm², respectively. The imaging plane is "switched" by tuning the frequency of the drive signal to change the scanner mode from Z-axis piston to Y-axis tilting. The resulting field of view (FOV) is exceptionally large for an endomicroscope, and is achieved using an optical design where the scanner is placed in the post-objective position.

Figures 7A, 7B:
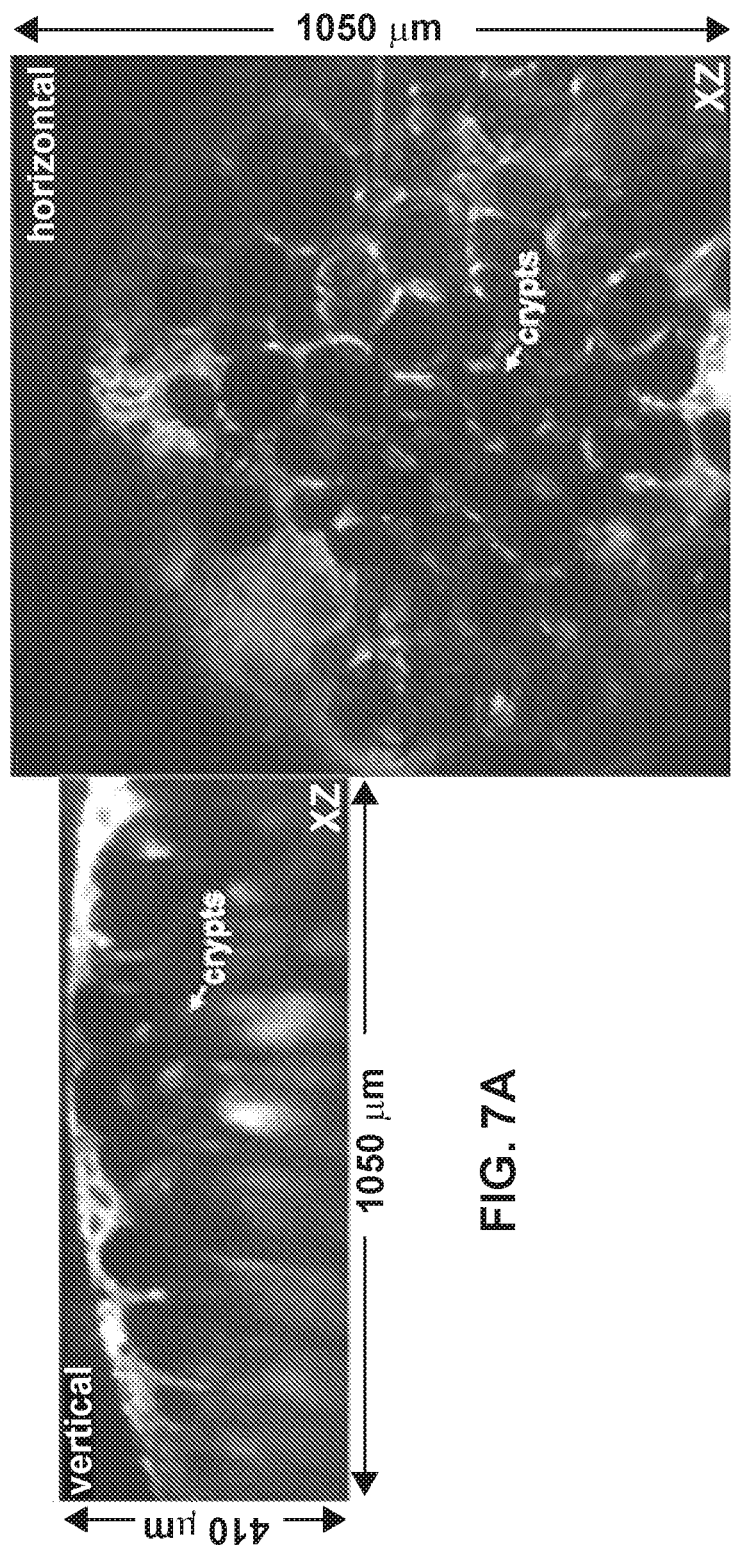
FIGS. 7A-7B are images of sample subject tissue images taken in a vertical plane (FIG. 7A) and a horizontal plane (FIG. 7B) in accordance with various embodiments.

FIG. 7A illustrates anatomic images of normal human colonic mucosa in the vertical plane to a depth of 410 μm where crypts are columnar in shape. The displacement is slightly less than a maximum displacement measured prior to packaging the scanner in the endomicroscope. Additionally, damping of scanner motion may occur when it is confined within the scanhead, depending in the designs. The mucosal surface appears slightly curved because post-objective scanning produces an arc-surface rather than a plane. FIG. 7B illustrates the same specimen viewed in the horizontal plane where the crypts are now circular in shape.

An integrated monolithic 3D MEMS scanner 110 is described that uses a lever-based gimbal-like structure to produce large angular deflections and axial displacements in 3D with scanning high speeds. The frequency response in the Z-axis has a stable high gain region that produced, in an example, a maximum axial displacement of approximately 510 μm. In an example, the scanner 110 is sized to package in a 10 mm diameter dual axes confocal endomicroscope, and is used to collect either vertical or horizontal cross-sectional images by tuning the drive frequency to "switch" between image planes. Fluorescence images with a large horizontal dimension of 1050 μm and depth of 410 μm in human colon were achieved ex vivo at low drive voltages. This depth is adequate to visualize the full epithelium of most hollow organs. The small chip size of approximately 3.2×2.9 mm² allows for used in a 5.5 mm endomicroscope that has previously been used in clinical testing.

This electrostatic scanner achieved motion amplitudes much larger than those of other devices of similar size by operating in a regime that features mixed softening/stiffening dynamics, see, e.g., FIG. 5. This scanner is an example of a parametrically resonant dynamic system in which a bifurcation in stable system dynamics occurs that results in continuous oscillation in response to periodic inputs near integer multiples of the system's structural resonance. The amplitude of oscillation increases as the frequency is reduced from high to low frequencies, reaching peak amplitude at approximately the structural resonance of the system. Further reduction in frequency results in rapid reduction and then disappearance of oscillations.

When mixed stiffening/softening dynamics are present, a secondary bifurcation can occur, allowing for larger oscillation amplitudes to be realized than that from the initial bifurcation. The existence of this bifurcation was previously anticipated in response to a sinusoidal drive for an in-plane electrostatic resonator. However, this secondary bifurcation can be realized at reduced voltages when applying low duty-cycle square waves. Under these circumstances, the spring stiffening effects of the silicon torsion springs that support the mirror help that of the 'on'-period of the square wave, and hence the electrostatic force, is synchronized with the restoring force generated by the springs. This results in larger scanning amplitudes than with sinusoidal or high duty-cycle square waves, in which a portion of the voltage 'on'-period acts in opposition to the restoring force of the springs.

The out-of-plane displacement (Z-axis) of the scanner may be limited by air damping when packaged in an endomicroscope, and may achieve significantly larger amplitudes in a vacuum. The scanner structure has a compact design that contains a large aperture mirror with high fill-factor. Furthermore, use of vacuum packaging in the scanhead may reduce air viscosity and lower pressure. By introducing a cavity in the mirror holder (see FIG. 6) by replacing the normal substrate with a flattened surface to reduce the squeeze number and the coefficient of viscous damping (or torque) of the squeeze film damping, large axial displacement with high scan speeds are achieved. This packaging strategy allows the compliant lever mechanism on the mirror gimbal to achieve unusually large stroke lengths for an electrostatic MEMS scanner at high scan speeds and in ambient pressure.

The present techniques and devices provide considerable advantages over conventional devices.

Figure 9:
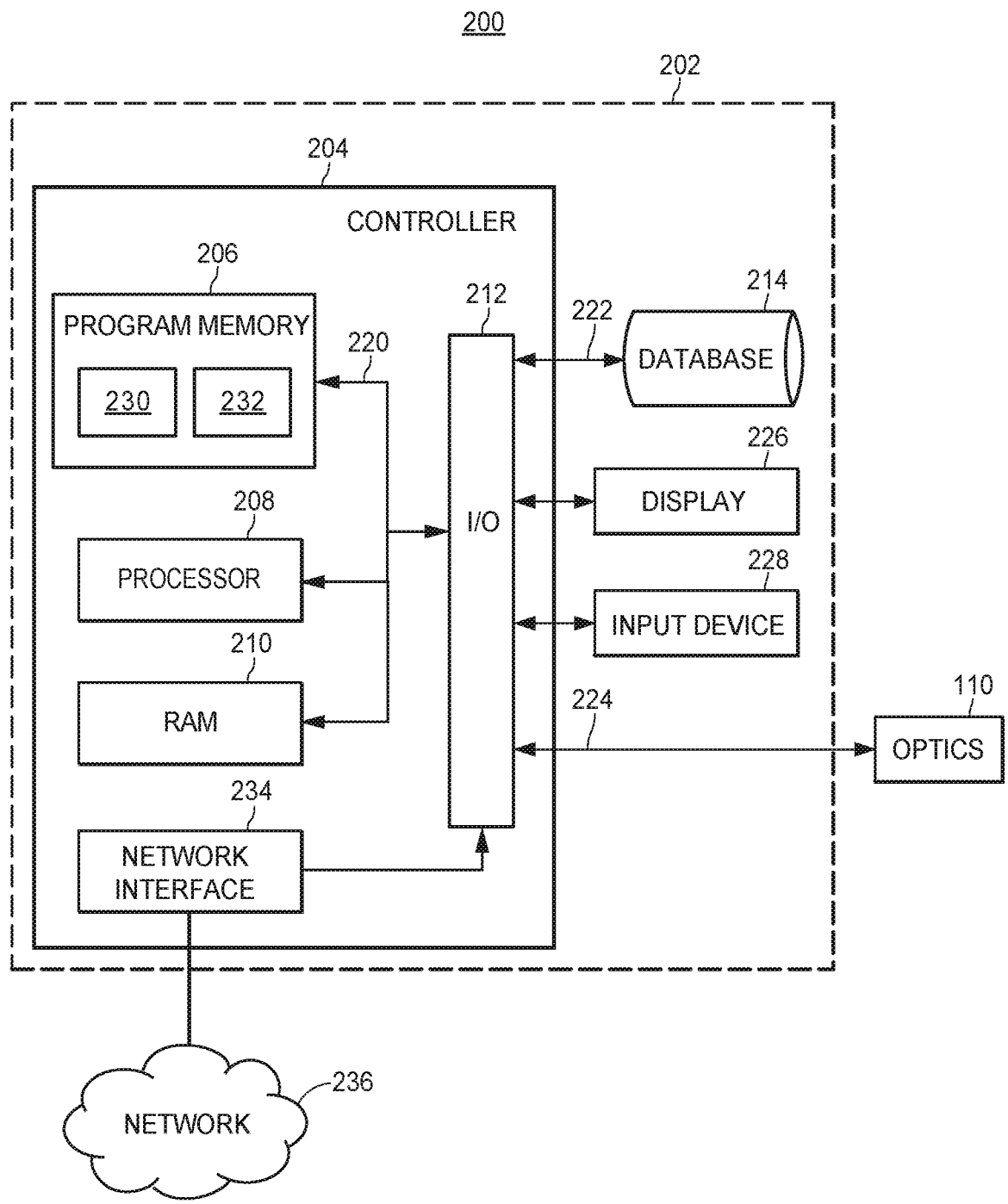
FIG. 9 depicts an example block diagram illustrating various components used in implementing an exemplary embodiment of the 3D MEMS scanner in accordance with various embodiments.

FIG. 9 is an example block diagram 200 illustrating the various components used in implementing an example embodiment of the 3D MEMS scanner discussed herein. The device 202 may have a controller 204 operatively connected to the database 214 via a link 222 connected to an input/output (I/O) circuit 212. It should be noted that, while not shown, additional databases may be linked to the controller 204 in a known manner. The controller 204 includes a program memory 206, the processor 208 (may be called a microcontroller or a microprocessor), a random-access memory (RAM) 210, and the input/output (I/O) circuit 212, all of which are interconnected via an address/data bus 220. It should be appreciated that although only one microprocessor 208 is shown, the controller 204 may include multiple microprocessors 208. Similarly, the memory of the controller 804 may include multiple RAMs 210 and multiple program memories 206. Although the I/O circuit 212 is shown as a single block, it should be appreciated that the I/O circuit 212 may include a number of different types of I/O circuits. The RAM(s) 210 and the program memories 206 may be implemented as semiconductor memories, magnetically readable memories, and/or optically readable memories, for example. A link 224 may operatively connect the controller 204 to the tip head of the optical fiber 108 through the I/O circuit 212.

The program memory 206 and/or the RAM 810 may store various applications (i.e., machine readable instructions) for execution by the microprocessor 208. For example, an operating system 230 may generally control the operation of the endomicroscope 202 and provide a user interface to the testing apparatus to implement the processes described herein. The program memory 206 and/or the RAM 210 may also store a variety of subroutines 232 for accessing specific functions of the endomicroscope 202. By way of example, and without limitation, the subroutines 232 may include, among other things: a subroutine for controlling operation of the 3D MEMS scanner 110, or other endoscopic device, as described herein; a subroutine for capturing images with the scanner 110 as described herein; a subroutine for exciting the gimbal assembly to scan the mirror in orthogonal directions in response to a control signal (also referred to as a drive signal herein) having a frequency; a subroutine for switching the mirror assembly from a flattened position to an erected position for scanning over a three-dimensional volume of the sample; a subroutine for providing the control signal at or near integer multiples of a structural resonance of the scanning assembly; a subroutine for providing the control signal having a Lissajous scan pattern (that is, a scan pattern corresponding to a Lissajous curve); a subroutine for parametrically exciting the mirror assembly for scanning; a subroutine for providing the control signal having a duty cycle chosen to drive the mirror assembly into scanning along one of a plurality of different orthogonal two-dimensional regions, where different duty cycles result in the scanning along different regions; and other subroutines, for example, implementing software keyboard functionality, interfacing with other hardware in the endomicroscope 202, etc. The program memory 206 and/or the RAM 210 may further store data related to the configuration and/or operation of the endomicroscope 202, and/or related to the operation of one or more subroutines. For example, the data may be data gathered by the scanner 110, data determined and/or calculated by the processor 208, etc. In addition to the controller 204, the endomicroscope 202 may include other hardware resources. The endomicroscope 202 may also be coupled to various types of input/output hardware such as a visual display 226 and input device(s) 228 (e.g., keypad, keyboard, etc.) to fine tune actuation of the axial and lateral scanners. In an embodiment, the display 226 is touch-sensitive, and may cooperate with a software keyboard routine as one of the software routines 232 to accept user input.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed:

1. An optical probe scanning assembly for use in an optical probe having a housing having a proximal end and a distal end positioned at a sample, the scanning assembly comprising:
    a mirror assembly configured to focus an illumination beam path and a collection beam path at a region of interest within the sample where the illumination beam and the collection beam overlap to form a confocal beam region, the mirror assembly being movable in an x-axis direction, a y-axis direction, and a z-axis direction to scan the confocal beam region within the sample; and
    a scanning suspension system comprising a gimbal assembly connected to the mirror assembly to cause the mirror assembly to rotate in the x-axis direction and the y-axis direction and to be movably displaced along the z-axis direction, such that the mirror is adapted to scan along at least two different orthogonal planes, one of which extends vertically into the sample along the z-axis direction.

2. The scanning assembly of claim 1, wherein the mirror assembly is configured to scan the confocal beam region across a three-dimensional volume in the sample.

3. The scanning assembly of claim 1, wherein the vertical scanning assembly is configured to scan the confocal beam region over a three-dimensional volume that extends from an vertical depth of the sample extending from an upper surface of the sample to a depth of at least 400 pm below the upper surface.

4. The scanning assembly of claim 3, wherein the vertical scanning assembly is configured to scan the confocal beam region to a depth of 400 pm below the upper surface of the sample.

5. The scanning assembly of claim 1, wherein the scanning suspension assembly further comprises:
    opposing lever arms disposed on each side of the mirror assembly and deflectable from a flattened position of the mirror to an erected position, each lever arm coupled to the mirror through a serpentine spring mechanism to allow for rotation of the mirror assembly when the mirror assembly is in the erected position.

6. The scanning assembly of claim 1, wherein the scanning suspension assembly further comprises:
    an inner spring assembly for scanning the mirror about a first axis; and
    an outer spring assembly for scanning the mirror about a second axis orthogonal to the first axis.

7. The scanning assembly of claim 1, further comprising a controller having a processor and a memory, the controller being configured with executable instructions (i) to excite the gimbal assembly to scan the mirror in orthogonal directions in response to a control signal having a frequency, (ii) to switch the mirror assembly from a flattened position to an erected position for scanning over a three-dimensional volume of the sample, (iii) to provide the control signal at or near integer multiples of a structural resonance of the scanning assembly, (iv) to provide the control signal having a Lissajous scan pattern, (v) to parametrically excite the mirror assembly for scanning, and/or (vi) to provide the control signal having a duty cycle chosen to drive the mirror assembly into scanning along one of a plurality of different orthogonal two-dimensional regions, where different duty cycles result in the scanning along different regions.

8. The scanning assembly of claim 1, wherein the mirror assembly comprises a micro-mirror having a first reflector pad for reflecting the illumination beam into the sample and a second reflector pad for reflecting the collection beam out of the sample.

9. The scanning assembly of claim 8, wherein the first reflector pad and the second reflector pad are connected by a strut to achieve dual movement of the first reflector pad and the second reflector pad.

10. The scanning assembly of claim 9, wherein the mirror assembly further comprises a comb drive capable of deflecting the micro-mirror for scanning the confocal beam region along one or more transverse directions.

11. The scanning assembly of claim 9, wherein the mirror assembly further comprises multiple comb drives that are collectively capable of deflecting the micro-mirror for scanning the confocal beam region along two orthogonal transverse directions.

12. The scanning assembly of claim 1, wherein the micro-mirror is a MEMS fabricated mirror.

13. The scanning assembly of claim 1, wherein the mirror assembly further comprises a mirror element.

14. The scanning assembly of claim 13, wherein the mirror element is a parabolic mirror.

15. The scanning assembly of claim 1, wherein the probe housing assembly has a diameter of approximately 10 mm or below.

16. The scanning assembly of claim 1, wherein the probe housing assembly has a diameter of approximately 5 mm.

17. The scanning assembly of claim 1, further comprising a controller having a processor and a memory, the controller being configured with executable instructions to:
   excite the gimbal assembly to rotate the mirror along the x-axis direction and the y-axis direction in response to a control signal having a first frequency; and
   displace the mirror assembly along the z-axis direction from a flattened position to an erected position for scanning over a three-dimensional volume of the sample in response to a control signal having a second frequency.

\* \* \* \* \*

UNITED STATES PATENT AND TRADEMARK OFFICE
CERTIFICATE OF CORRECTION

PATENT NO. : 10,642,027 B2
APPLICATION NO. : 15/781065
DATED : May 5, 2020
INVENTOR(S) : Thomas D. Wang et al.

It is certified that error appears in the above-identified patent and that said Letters Patent is hereby corrected as shown below:

In the Claims

At Column 14, Line 8, "400 pm" should be -- 400 µm --.

At Column 14, Line 12, "400 pm" should be -- 400 µm --.

Signed and Sealed this
Nineteenth Day of January, 2021

Andrei Iancu
*Director of the United States Patent and Trademark Office*